United States Patent [19]

Tester

[11] 4,185,973
[45] Jan. 29, 1980

[54] WASTE DISPOSAL SYSTEM

[75] Inventor: Colin A. Tester, Pinner, England

[73] Assignee: Metal Box Limited, Reading, England

[21] Appl. No.: 891,323

[22] Filed: Mar. 29, 1978

[30] Foreign Application Priority Data

Apr. 1, 1977 [GB] United Kingdom ............... 13780/77

[51] Int. Cl.² ............................................. B01D 51/00
[52] U.S. Cl. ....................................... 55/212; 55/419; 55/420; 241/33; 241/59; 241/DIG. 38
[58] Field of Search ...................... 210/152, 173, 174; 55/212, 418–420; 241/33, 59, 47, 75, 79, DIG. 38

[56] References Cited

U.S. PATENT DOCUMENTS

| 4,032,446 | 6/1977 | Miller, Jr. | 210/173 |
| 4,037,795 | 7/1977 | Fyfe | 241/DIG. 38 |

FOREIGN PATENT DOCUMENTS

455604  10/1936  United Kingdom .................... 210/173

Primary Examiner—John Adee
Attorney, Agent, or Firm—Diller, Ramik & Wight

[57] ABSTRACT

In a waste disposal system (e.g. in a hospital) in which at least one shredding machine comminutes waste which is then drawn by air suction through a closed ducting system for destruction, each shredder has a discharge valve associated with its waste outlet, this valve being normally open but partially or wholly closed when the shredder is opened to receive waste; the shredder also has a vent opening in its waste inlet door to relieve pressure, and internal germicide sprays.

9 Claims, 13 Drawing Figures

WASTE DISPOSAL SYSTEM

This invention relates to waste disposal systems comprising at least one shredding machine, and to shredding machines in or for such systems, the shredding machines being of the kind having a sealably closable waste input aperture, an enclosed comminuting mechanism for comminuting waste received through said aperture, and a waste outlet for the waste so comminuted (a shredding machine of this kind being referred to herein as a "shredder of the kind hereinbefore specified"), the waste disposal system further comprising: treatment apparatus for the comminuted waste; an air inlet; ducting connecting the air inlet with the treatment apparatus and connected also with the said waste outlet or outlets intermediate between the air inlet and the treatment apparatus; and air suction means for drawing the comminuted waste from the or each shredder and through the ducting into the treatment apparatus. Such a system will be referred to herein as a "waste disposal system of the kind hereinbefore specified".

Such a system is particularly suitable for installation in a hospital; and the remainder of this specification will be concerned mainly with hospital waste disposal systems and with comminuting machines adapted for use therein. However, it is to be understood that such systems, including those according to the invention as set out and described hereinafter, may be employed in, for example, laboratories, factories, blocks of flats and on any other site in which comminutable waste matter is discarded in one or more places on the site and destroyed, or otherwise treated, in another part of the site. In particular, waste disposal systems of the kind hereinbefore specified are desirable where the waste matter consists of, or includes, actually or potentially toxic, injurious or otherwise objectionable matter.

It is highly desirable to destroy such matter or at least to render it harmless, as quickly as possible. Therefore it has hitherto been proposed to provide waste disposal systems of the kind hereinbefore specified to enable treatment to take place on site (so avoiding the need for transport of harmful waste), whilst at the same time placing the treatment apparatus at a location remote from working areas (such as hospital wards) and enabling the waste to be discarded actually in or adjacent to the working areas themselves. Thus in a large hospital there may be one shredder to each ward, and others associated with the pathology department, kitchens, operating theatres, out-patient clinics and so on. All these shredders feed into the common ducting system.

It will be obvious that among the prime requirements of such a system are that bacteria, fumes and smells derived from the waste matter must not escape from any part of it; that the shredders must be such that they can be kept clean at all times, and readily sterilized, and must be so arranged that when the loading ports are opened there is no danger to, or escape of noxious matter towards, the person loading the shredder; and that a sufficiently powerful suction force must be available in the system to ensure that, whenever a shredder is operating, the waste material discharged from the shredder will be quickly and reliably transported through the ducting to the treatment apparatus. To provide a sufficient mass flow of air to transport the waste matter through the system, an air inlet is provided, in a suitable and safe position, in an upstream extremity of the ducting.

In a waste disposal system of the kind hereinbefore specified having two or more shredders (hereinafter called a "multi-station system"), it will be realised that it is theoretically possible for the loading ports of both or all of the shredders to be open simultaneously. The greater the number of stations, the greater the number of points at which, under such circumstances, air can enter the system. The suction means abovementioned, i.e. an exhauster, must be made sufficiently powerful to maintain adequate suction even under these worst conditions. Particularly in a multi-station system for a unit such as a large hospital, where there may be many shredders, this may prove uneconomic.

According to the invention in a first aspect, a waste disposal system of the kind hereinbefore specified includes a discharge valve interposed, in respect of the or each said shredder, between the comminuting mechanism on one side of the discharge valve and, on its other side, said air inlet and treatment apparatus, the or each discharge valve being arranged to be at least partially closed so long as the waste input aperture of the shredder associated therewith is open.

The (or each) discharge valve thus at least partly closes off the remainder of the system from the associated shredder when the waste input aperture of the latter is open. This has several advantageous effects, the most important of which is that it prevents the opening of a waste input aperture from substantially reducing the suction in the system and, particularly, prevents any shredders upstream of the one concerned being noticeably affected by any reduction of air suction due to air being drawn in through the input aperture of that shredder.

Preferably, however, the or each discharge valve is arranged to provide incomplete sealing such that it still permits a small air flow to occur into the associated shredder, whilst providing sufficient sealing not to reduce the suction in the remainder of the system to an unacceptable degree. This small air flow will be arranged to be sufficient to ensure that, whilst the waste input aperture is open, no air will escape from the shredder with possible harmful effects on the operator due to the bacteria or other toxins, or to noxious smells.

In one possible arrangement of a system according to the invention, the ducting comprises a main stack leading generally downwardly from said air inlet, the waste outlet of the or each shredder being connected to the main stack without being interposed between the air inlet and the treatment apparatus, and the associated discharge valve being interposed between the respective comminuting mechanism and the main stack. In an alternative arrangement, in which the discharge valve of the or each shredder is interposed between the comminuting mechanism and waste outlet thereof, the or each shredder is interposed in the ducting intermediate between the air inlet and the treatment apparatus, so as to be scavenged by air passing from the former toward the latter.

According to the invention, in a second aspect, there is provided in or for a waste disposal system according to said first aspect of the invention, a shredder of the kind hereinbefore specified having an enclosing hollow body defining the waste input aperture, the comminuting mechanism being within said hollow body and the waste outlet leading from within said body below the level of the comminuting mechanism, wherein a discharge valve, movable between an open position and an at least partially closed position, is carried by said hollow body at a level below that of the comminuting mechanism, and the body has a door for sealably closing said input aperture.

The discharge valve may be mounted in the waste outlet, or within the hollow body above the level of the waste outle.

Preferably, the waste input aperture is sealably closeable by a door having a vent aperture and a vent flap for sealably closing the vent aperture, the vent flap being arranged for opening and closing independently of opening and closing of the door.

The vent aperture provides a small opening to atmosphere to break the partial vacuum that exists in the interior of the shredder when the door, which normally sealingly closes the waste input aperture, is closed. This enables the input aperture itself to be opened more easily and without requiring a substantial force to break the seal.

The shredder preferably includes spray means positioned for directing germicidal spray inwardly of the hollow body, the spray means being mounted therein adjacent the input aperture.

Various embodiments of the invention will now be described, by way of example only, with reference to the accompanying drawings, of which:

FIG. 10, which is in four parts, viz. FIG. 10(*a*), 10(*b*), 10(*c*) and 10(*d*), each being a simplified sectional side elevation of the shredder, illustrates four steps in the said sequence of operation.

Figure 1:
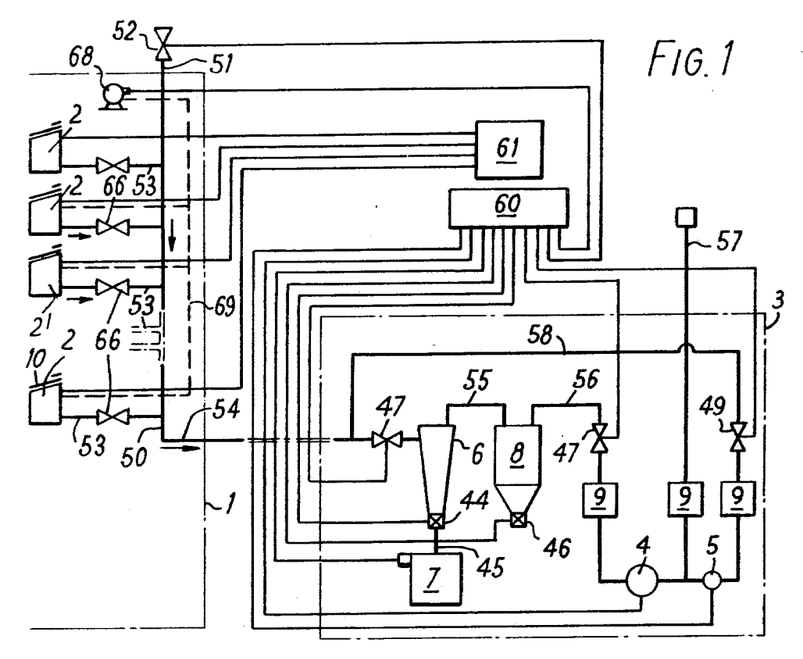
FIG. 1 is a simplified schematic diagram showing principal components of a multi-station waste disposal system in one embodiment of the invention, for hygienically removing and treating contaminated waste from a hospital.

Referring to FIG. 1, a hospital building 1 has a number of storeys housing wards, operating theatres, laboratories, kitchens, laundry, offices, mortuary, stores etc. At one or more convenient places on each floor, there is located a waste shredder 2. For simplicity, FIG. 1 shows one shredder 2 on each of four of the floors. Members of the hospital staff can dispose of certain kinds of refuse by opening a waste input aperture door or inlet port cover 10, provided on each of the shredders 2, and dropping the refuse into the shredder.

The kinds of refuse disposed of in this way are those which are suitable for shredding into small pieces, and which consist mainly of solid matter, though some liquid content is quite acceptable. Examples include soiled dressings, bags, small or medium cartons, used hypodermic syringes of the disposable type, hypodermic needles, ampoules, disposable scissors and other disposable implements.

The waste disposal system of the hospital comprises the shredders 2; treatment apparatus for waste comminuted in the shredders 2, the apparatus being located in a separate building 3, on the hospital site but safely remote from the hospital building 1; an air inlet 51; ducting which is indicated by heavy full lines in FIG. 1; and which connects the air inlet 51 with the treatment apparatus, the ducting being also connected with waste outlets of the shredders 2, intermediate between the air inlet and the treatment apparatus; and air suction means 4, 5 for drawing the comminuted waste from the shredders 2 and through the ducting into the treatment apparatus by air suction.

The treatment apparatus comprises a centrifugal separator 6; an incinerator 7; a dust filter 8; and bacteriological air filters 9. The ducting includes a vertical main stack 50, extending generally downwardly through the hospital building 1 from the fresh-air inlet 51 above the roof of the building. The air inlet 51 has an electrically-operated inlet valve 52, the purpose of which will be explained hereinafter. The waste outlet of each of the shredders 2 is connected with an outlet branch 53 which leads into the main stack 50 (so that, in this embodiment, the shredders are not interposed between the air inlet 51 and the treatment apparatus). The lower end of the stack 50 is connected with a main duct 54 leading into the treatment apparatus building 3.

The remainder of the ducting connects together the suction means 4, 5 and the various components of the treatment apparatus. The suction means consist of a main exhauster 4 situated downstream of the dust filter 8, and a secondary exhauster 5.

The main duct 54 leads into the separator 6, which has a hopper discharging through a discharge valve 44 into the incinerator 7. The separator 6 has an air outlet connected with the dust filter 8, which has a discharge valve 46 and an air outlet, the latter being connected by a duct 56 with the suction side of the main exhauster 4. The delivery side of the latter is connected with a vertical exhaust stack 57 discharging into the atmosphere. The secondary exhauster 5 is connected in a bypass duct 58, one end of which is connected to the main duct 54 upstream of the separator 6, the other end, on the delivery side of the secondary exhauster 5, being connected to the exhaust stack 57. Two isolating valves 47 are so disposed in the ducting that, when both are open, the main stack is in series communication with the suction side of the main exhauster 4 through the separator 6 and dust filter 8, whilst a bypass valve 49 is provided in the bypass duct 58. A main electrical control unit, indicated diagrammatically at 60, is situated in the plant building 3, or elsewhere as appropriate. It supplies control signals for actuating various electrically operated components of the treatment apparatus, for the exhausters 4 and 5, and for the fresh air inlet valve 52. The power supply to each shredder 2 is from the mains and controlled by a shredder control unit indicated diagrammatically at 61, which is linked electrically with the main control unit 60 for purposes to be described.

Referring now to FIGS. 2 to 5, the shredder shown therein has a waste input aperture or inlet port 14 defined by an enclosing hollow body, the latter comprising a loading chute 23, a shredder box 11 and a hopper 30. The shredder also has a smooth, hygienic stainless steel outer casing 12 having a sloping top 13 around the inlet port 14. The inlet port 14 is closed by the hinged door 10, which has a peripheral seal 17 so that, when closed, the cover hermetically seals the shredder around the inlet port 14 so as to close the latter fully. The shredder has an internal frame 18 carrying the hopper 30, which has a waste outlet port 19 for connection to the branch duct 53. Above the hopper 30, and communicating therewith, the shredder box 11 is carried by the frame 18 and contains the comminuting mechanism of the shredder. The latter comprises a pair of parallel, contra-rotating rotors 15, each of which consists of a shaft 20 carrying a number of cutters 21 so arranged (in a manner well-known in the art) that the cutters of one rotor 15 are interleaved with those of the other rotor, and co-operate therewith to shred (comminute) wast fed on to the rotors from above. The rotors 15 are driven, through a suitable gearbox and clutch (not shown), by an electric motor 22, shown in FIG. 3 but not in FIG. 2 an mounted within the casing 12.

Figure 3:
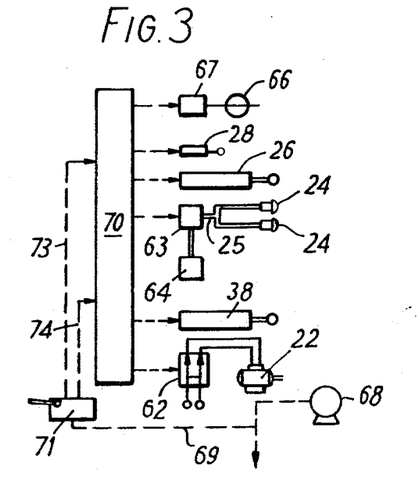
FIG. 3 is a diagrammatic representation of a pneumatic control circuit of the shredder.

The motor 22 is controlled by a pneumatically-operated circuit breaker 62, FIG. 3, which is actuated in a manner hereinafter to be described.

Figure 4:
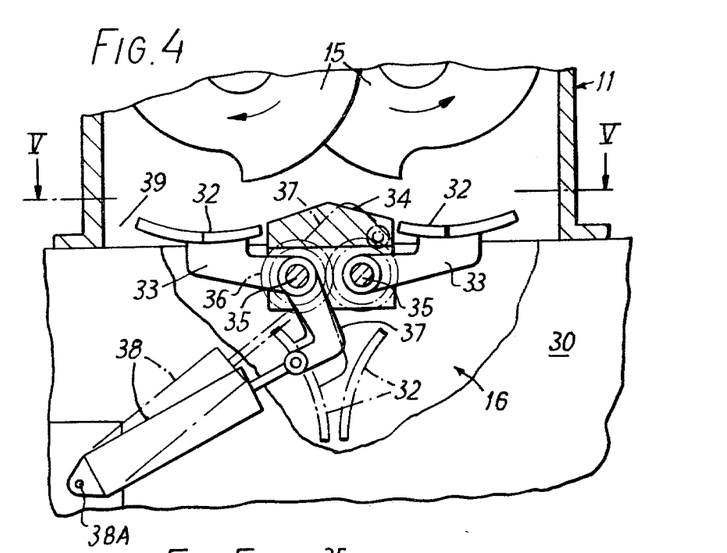
FIG. 4 is a partly cut-away sectional side elevation of part of the shredder, on a larger scale than FIG. 2.
Figure 5:
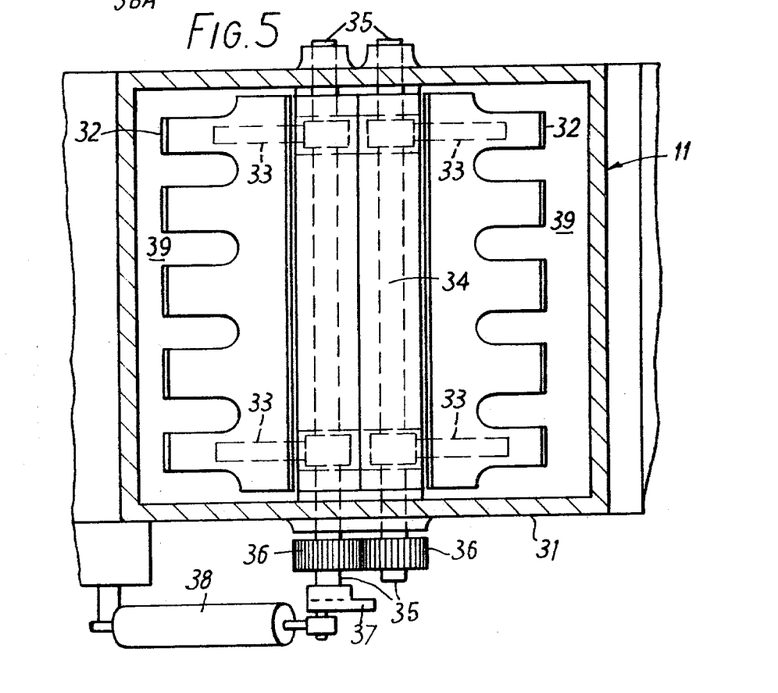
FIG. 5 is a plan view taken generally on the line V—V in FIG. 4.

Below the rotors 15 and at the bottom of the shredder box 11 is a retractable grid assembly 16, shown in more detail in FIGS. 4 and 5. In FIG. 4, part of the side wall 31 of the hopper 30 is shown cut away to reveal the grid assembly.

The grid assembly 16 includes a pair of grid plates 32 each carried by arms 33. In the operative position shown in full lines in FIGS. 2, 4 and 5, the grid plates 32 lie parallel to, and on either side of, a deadplate 34 carried by the frame 18 and having its centre line in the vertical mid-plane between the axes of the rotor shafts 20. The arms 33 are fixed to a pair of shafts 35, rotatable in the frame 18 and coupled by a pair of equal pinions 36. One of the shafts 35 has fixed to it a crank 37 coupled to a pneumatic actuator 38. The latter is pivoted to the shredder frame 18 at its lower end 38A.

In normal operation of the shredder, comminuted waste is urged laterally from the deadplate 34, over the grid plates 32, to be discharged through gaps 39 at the sides of the shredder box 11 into the hopper 30.

To clear the shredder of large and/or jammed pieces of waste matter, the actuator 38 is operated to rotate the shafts 35 and so move the grid plates 32 to the open position shown in chain-dotted lines in FIG. 4, in which position they are clear of the path of any material being drawn downwardly from the shredder box 11.

Figures 2, 7, 8:
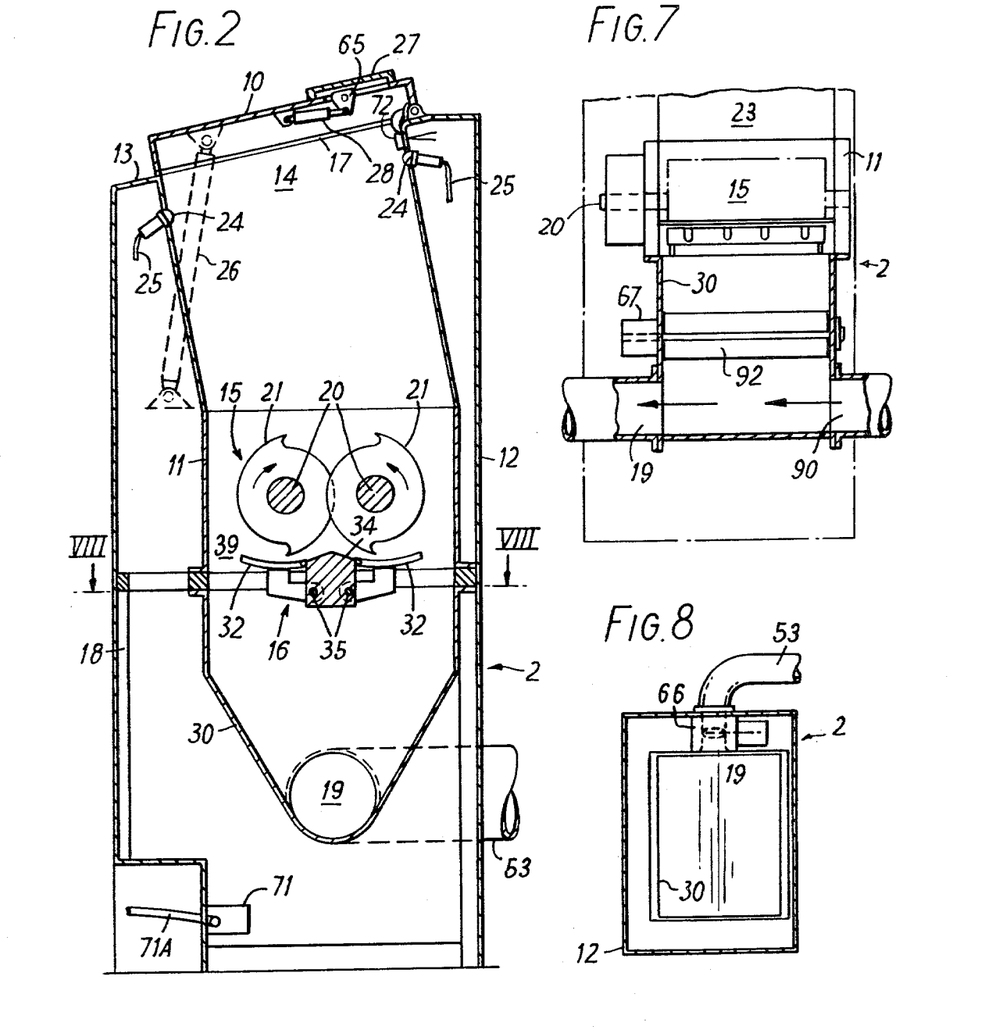
FIG. 2 is a simplified sectional side elevation of one shredder forming part of the system shown in FIG. 1.
FIG. 7 is a diagrammatic sectional rear elevation of part of one of the shredders of FIG. 6.
FIG. 8 is a simplified sectional plan view taken on the line VIII—VIII in FIG. 2.

Joining the inlet port 14 to the shredder box 11 is a loading chute 23, provided with spray heads 24 which are positioned, for directing a germicidal spray inwardly of the loading chute 23, adjacent to the inlet port 14. The spray heads 24 are connected, through pipes 25, with a pneumatic control valve 63 (FIG. 3), through which they can be supplied with liquid germicide solution under pressure from a reservoir 64 (FIG. 3). This reservoir may be situated within the shredder casing 12 or outside it, as desired. In one suitable arrangement, the reservoir 64 is a container of concentrated gericide with suitable means, connected with a continuous water supply, for metering predetermined quantities of germicide and water, and for mixing them (all in known manner) for delivery through the valve 63 to the spray heads 24 when the valve 63 is open.

The inlet port cover 10 is operated by a simple pneumatic actuator 26, pivoted at its lower end to the shredder frame 18. The shredder also has a vent aperture 10A closed by a small vent flap 27 arranged to be opened independently of the inlet port itself; the flap 27 is hinged to the cover 10 and, in its closed position as shown in FIG. 2, covers and sealing the vent hole 10A. The vent flap 27 is operated, independently of the operation of the inlet port cover 10, by any suitable means; in this example it is operated by a small cam 65 controlled by a pneumatic actuator 28.

Referring once again to FIG. 1, there is provided in each ducting branch 53 (and thus downstream of the shredder outlets) a discharge valve 66. Each of these valves, being thus positioned, is interposed between the comminuting mechanism 15 of the corresponding shredder on the side of the valve, and, on its other side, both the fresh air inlet 51 and the treatment apparatus of the waste disposal system. Thus, closing of any one of the discharge valves 66 does not interrupt the flow of air through or from any of the shredders 2 except that one with which it is associated. Each discharge valve 66 is preferably a simple flap valve arranged to vary the cross-sectional area of the ducting branch 53 in which it is situated, between a fully-open first position and a second position in which the valve nearly, but not quite, shuts off the duct.

Each discharge valve 66 is actuated by a pneumatic or electrical valve actuator. Preferably, however, these valve actuators are pneumatic and are controlled from a pneumatic control system of the associated shredder 2 itself. Such a control system is shown diagrammatically in FIG. 3, the discharge valve actuator being indicated therein at 67. Compressed air for the pneumatic control system of the various shredders 2 is supplied by a small common air compressor 68, FIGS. 1 and 3, through pipes 69 indicated in FIG. 1 by broken lines.

Each shredder 2 has a pneumatic sequential control unit 70, arranged according to known principles (for example employing fluidic circuitry) to operate the germicidal spray control valve 63, the grid plate actuator 38, the inlet port cover actuator 26, the venting flap actuator 28, the discharge valve actuator 67, and the motor circuit breaker 62. The sequence of operation of these components will be described hereinafter with reference to FIGS. 9 and 10; at this point it is sufficient to mention that the control unit 70 operates automatically to follow a predetermined sequence upon initiation of the latter by operation of a pedal switch 71 mounted in the bottom of the shredder casing 12.

In addition, an electrical microswitch 72 (FIG. 2), responsive to opening of the inlet port cover 10, is connected through the shredder control unit 61 (FIG. 1) with the main control unit 60, the latter being arranged to start the main exhauster 4 whenever a signal from any one of the microswitches 72 of the various shredders 2 indicates opening of the inlet port 14 of that shredder.

It should be emphasised that, when the vent flap 27 and inlet port cover 10 are closed, the interior of the shredder within the loading chute 23, shredder box 11 and hopper 30 constitutes a chamber sealed everywhere except at the outlet 19. Components such as shaft bearings, mounted in the shredder box sidewalls, are of the gas-tight kind.

Figure 6:
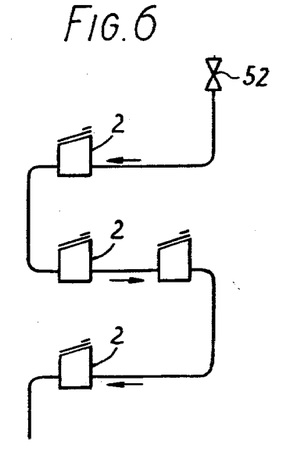
FIG. 6 is a diagram illustrating as an alternative to that shown in FIG. 1, a modified mode for connecting shredders in the waste disposal system.

Whereas in FIG. 1 the shredders are shown connected to a main stack 50 by individual ducting branches 53, they may alternatively be interposed in the ducting intermediate between the air inlet 51 and the treatment apparatus, so as to be scavenged by air passing from the air inlet towards the treatment apparatus. For example, the shredders may be connected in series with each other in the manner shown in FIG. 6. Such shredders are modified by the addition of an air inlet 90 to the hopper, opposite the outlet 19, FIG. 7. In a series-connected system such as this, the discharge valve is located below the level of the comminuting mechanism and above that of the inlet 90 and outlet 19; and in the particular example illustrated diagrammatically in FIG. 7, the discharge valve comprises a pivoted plate 92, mounted in, and extending across, the hopper 30 parallel to the rotor shafts 20, and movable between the fully-open position shown and a wholly- or partially-closed position blocking off the hopper 30.

FIG. 8 illustrates a further modification to a shredder which is arranged for connection to a ducting branch 53, rather than for series connection, and in which the discharge valve 66 is arranged within the shredder casing 12 and in the hopper outlet 19. FIG. 8 illustrates the partially-closed position of the discharge valve, mentioned earlier herein.

Figure 9:
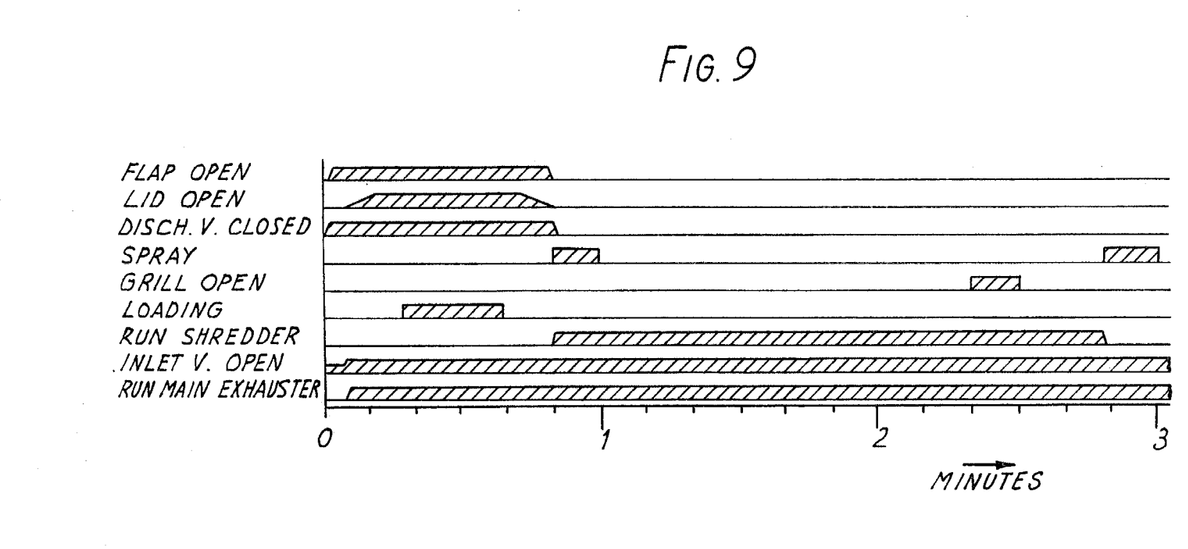
FIG. 9 is a diagram illustrating a sequence of operation of various components of a shredder according to the invention.

The operation of the waste disposal system described with reference to FIGS. 1 to 5 will now be described with particular reference to FIGS. 9 and 10.

Assuming that, initially, none of the shredders 2 is in use, but that the system is ready for operation, the state of the various components of the system is initially as follows. The vent flap 27 and inlet port cover 10 of each shredder is closed, the rotors 15 are stationary, and the grid plates 32 are in their operative or upper position. The germicidal spray heads 24 are not operating, and the discharge valves 66 are all fully open. The fresh air inlet valve 52 is partly open, but the isolating valves 47 are closed. The main exhauster 4 is not operating, but the by-pass valve 49 is open and the secondary exhauster 5 is running. This ensures that suction is maintained in the main stack 50, branches 53, shredders 2, main duct 54 and bypass duct 58, in all of which a predetermined air pressure, less than atmospheric pressure, is maintained by virtue of the fresh air inlet valve 52, whose degree of opening for this purpose is pre-set at the main control unit 60 to be effective whilst the secondary exhauster 5 is running. The air discharged from the exhauster 5 passes to atmosphere via the stack 57. The incinerator 7 may during this time be burning waste previously received from the shredders.

Suppose now a nurse wishes to dispose of an infected dressing (which she will have put into a plastic bag). She goes to the nearest shredder, say that indicated at 2' in FIG. 1. She applies her foot to the pedal 71A of the pedal switch 71, FIG. 10(a). This opens the pedal valve 71 to admit compressed air to the pneumatic control unit 70 of the shredder (FIG. 3). The control unit 70 now automatically initiates and controls the operation of the shredder, over an actual or nominal three-minute cycle illustrated diagrammatically in FIG. 9. In FIG. 9 the hatched areas represent, on a time base, the existence of the various states indicated in the column on the left-hand side of the Figure.

Figure 10A:
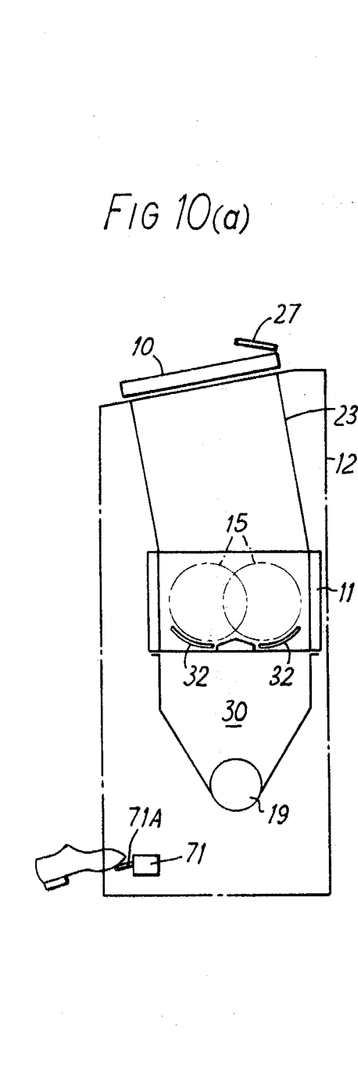

The cycle commences with closing of the discharge valve 66 to its nearly-closed position, whereupon the vent flap 27 is opened as seen in FIG. 10(a). This causes the air pressure inside the shredder to increase to a value which, because the discharge valve 66 is not quite closed, is still a little below atmospheric pressure but high enough to permit the inlet port cover 10 to open easily. The control unit 70 next operates the cover actuator 26 to raise the inlet port cover. As the latter starts to open, it operates the microswitch 72 to transmit an electrical signal to the main control unit 60.

Upon receipt of this signal, the main control unit transmits appropriate electrical signals which perform the following operations. The fresh air inlet valve 52 is opened to its fullest extent, so as to enable an increased mass flow of air to pass down the main stack 50. The isolating valves 47 are opened and the main exhauster 4 is started. The bypass valve 49 is then closed and the secondary exhauster 5 is stopped.

Figure 10B:
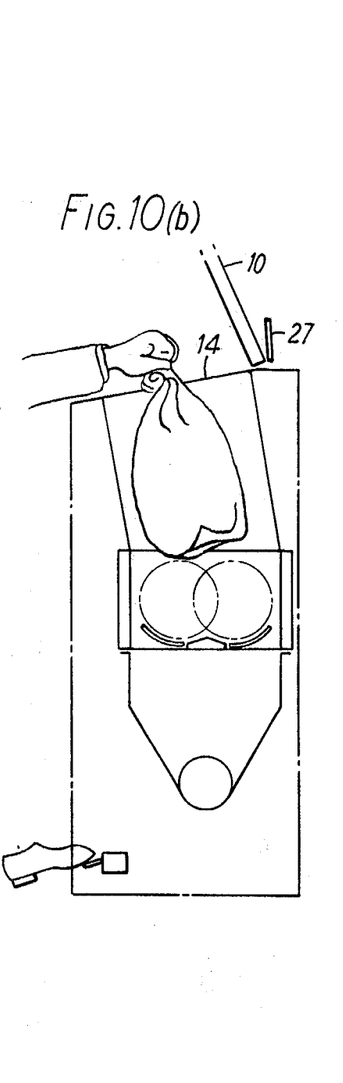

The shredder control unit 61 may include a suitable time delay device whereby the inlet port cover 10 is now held open for about half a minute, during which time the nurse can load the shredder by dropping into the loading chute 23 her infected dressing, FIG. 10(b). She can then remove her foot from the pedal 71A and depart. However, in a simpler arrangement the above-mentioned time delay device is absent and the cycle is continued, after loading has taken place, by release of the pedal 71A. In this latter case, of course, the total duration of the cycle depends on the time for which the inlet port cover 10 is held open under control of the pedal. The pedal switch 71 and control unit 70 are in this case suitably adapted so that when the pedal is depressed, compressed air is admitted to the control unit along one control path in a "starting" mode to perform the operations already described, whilst upon release of the pedal the air supply is diverted to the control unit along another control path, in a "stopping" mode, to perform the remainder of the cycle. It is this latter embodiment that is indicated in FIG. 3, in which the two paths abovementioned are indicated at 73 and 74.

The pedal switch 71 may if desired be so coupled with the pneumatic control unit 70 as to be opened upon completion of the shredder cycle. Alternatively, and preferably, it may be arranged so that the control unit 70 is in communication with the compressed air supply at all times, thus holding the shredder components, controlled thereby, positively in their rest positions from the termination of one cycle until the next is initiated by depression of the pedal 71A.

Figure 10C:
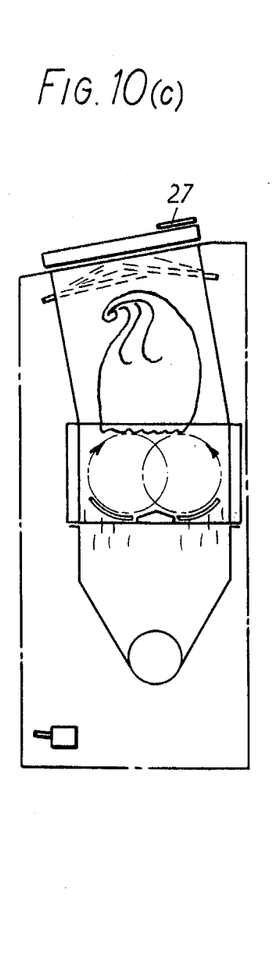

After the shredder has been loaded, then, the control unit 70 operates the actuator 26 to close the inlet port cover 10. It should be noted that when the latter, upon closing, engages the microswitch 72, the main control unit 60 does not stop the main exhauster 4; the latter continues running. As the cover 10 closes, the venting flap 27 is closed. As soon as the inlet port 14 is sealed, the discharge valve 65 is opened, and at the same time the spray valve 63 is opened and held open for ten seconds to drench the underside of the cover 10, and the walls of the loading chute 23, with germicidal spray, as shown in FIG. 10(c). This spraying operation, at this stage in the cycle, is performed so as to safeguard an operator who might re-open the inlet port 14 before the end of the shredder cycle, and thereby risk contamination of his or her clothing, particularly at the sleeves.

Figure 10D:
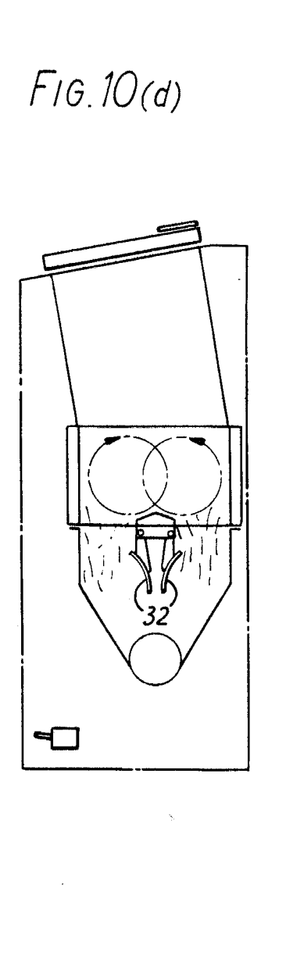

At the same time as the cover 10 reaches its fully-closed position, the pneumatic control unit 70 opens the circuit breaker 62 to run the shredder motor 22 for two minutes. The cutters 21 shred the waste matter delivered in the loading chute 23, the shredded waste dropping into the hopper 30. Over a ten-second period, commencing about half a minute before the end of the two-minute shredding period, the grid plates 32 are dropped in the manner described hereinbefore and as shown in FIG. 10(d), by operation of the actuator 38. This ensures that, by the end of the operating cycle, the shredder is completely free of waste matter. At the end of the above-mentioned two-minute period, the circuit breaker 62 is opened, and at the same time the germicide sprays 24 are again operated for a further ten seconds to complete the cycle. The shredder is now ready for commencement of a new cycle of operation.

Under the control of the main control unit 60, the main exhauster 4 draws the shredded waste from the shredder, down the main stack 50 and along the main duct 54 into the separator 6, which is designed so as to separate the solid matter from the airstream, the latter passing through the dust filter 8 whilst the solid matter falls into the separator hopper 43. Finally the air stream passes through the exhauster 4 and exhaust stack 57 to atmosphere.

If no further shredder has commenced an operating cycle by the end of a predetermined period sufficient to discharge into the exhaust stack 57 all the transport air from the cycle just described, the main control unit 60 now stops the main exhauster 4 and reverts the system to its initial state, with suction being maintained by the secondary exhauster 5. The main control unit 60 is provided, in known manner, with a suitable timer for this purpose, the timer being arranged to be reset to the start of its timing operation whenever a signal is received from any one of the shredder microswitches 72, indicating opening of an inlet port 14. Thus, if waste and/or transport air from one shredder is still being processed in the treatment apparatus when another shredder is operated, the main exhauster 4, separator 6 and dust filter 8 will continue to operate so long as they are needed, or until the hopper of either the separator 6 or the dust filter 8 is full. When this happens, however, it is necessary to interrupt the operation of the system, in order to empty the full hopper, by opening the bypass valve 49, closing the isolating valves 47 and starting the secondary exhauster 5 to maintain suction in the system. The fresh air inlet valve 52 is partially closed accordingly. The hoppers can then be emptied by operation of the appropriate dump valve 44 or 46.

Under certain circumstances, it may be necessary to delay operation of a selected one or more of the shredders. These circumstances include simultaneous discharge of waste matter into the ducting by more than a predetermined number of shredders, leading to excessive accumulation of shredded waste in the main stack 50; and closure of the isolating valves 47 for more than a predetermined time.

To this end, there may for example be provided an electro-pneumatic switch (not shown) associated with the pedal switch 71 of each shredder and arranged to over-ride the effect of depressing the pedal 71A, each of these electro-pneumatic switches being electrically controlled by a suitable selective timing device in the main control unit 60, arranged so that a predetermined delay in operation is applied to each shredder in turn. Preferably the shredders have warning light (not shown) which is illuminated during this delay time to indicate that the operator must wait. Total shutdown of the shredders can, if necessary for any reason, be effected by the main control unit 60 being provided with means for directly operating the said electro-pneumatic devices, in a manner over-riding the selective timing device, in response to a signal from a suitable sensor indicating a condition in the system calling for total shutdown.

The waste disposal system above described provides a hygienic, non-toxic, odourless means for disposing of hospital waste matter. Use of pneumatic controls in the shredders ensures the minimum of noise in the operation of the inlet port covers and other components. The shredder casings are in addition preferably lined with sound insulating material to reduce the noise of the motor and cutter operations. Even when the shredder venting ports 10A and inlet ports 14 are open, the air pressure within the system (except in the case of a complete blockage in the ducting or failure of both exhausters) is always less than atmospheric; and any flow of air, even in the event of a leak developing, is always into the system, apart from the discharge of pure air from the exhaust stack 57. Blockage of any air passage or failure of either exhauster will cause the shredders to remain closed and therefore sealed. In addition, the fresh air inlet valve 52 may be arranged to be closed in this eventuality.

I claim:

1. In a waste disposal system comprising a plurality of shredders having sealably closable waste input aperture means, enclosed comminuting means associated therewith for comminuting waste received therethrough, and waste outlet means for the waste so comminuted; treatment apparatus for the comminuted waste; a common air inlet means independent of the shredders; ducting connecting said common air inlet means with said treatment apparatus; means connecting the waste outlet means of each said shredder with said ducting, intermediate between said common air inlet means and treatment apparatus, in parallel with the means connecting the waste outlet means of the other shredder or shredders with said ducting; said treatment apparatus comprising air suction means for drawing transport air from said common inlet means at all times, and said comminuted waste from the shredders, and for drawing said air and waste through said ducting into the treatment apparatus, discharge valve means of the flow-regulating type arranged in the said means connecting the waste outlet means of each shredder with said ducting, and means for maintaining the discharge valve means partially closed so long as said waste input aperture means are open.

2. A waste disposal system according to claim 1, wherein the ducting comprises a main stack leading generally downwardly from said common air inlet, and a branch connecting each said waste outlet, said branches being in parallel with each other, to said main stack, each of said discharge valves being interposed in the respective said branch.

3. A waste disposal system according to claim 1, wherein each shredder has connecting means connecting it directly into said common ducting, comprising an inlet leading from said common inlet and an outlet leading to said treatment apparatus, the associated said discharge valve being interposed between the comminuting mechanism of said shredder and said connecting means.

4. A waste disposal system according to claim 1, wherein the discharge valve of each shredder is in the waste outlet thereof.

5. A waste shredder comprising a hollow body defining a waste input aperture, an openable door sealably closing said input aperture, means defining a waste outlet of said hollow body, a comminuting mechanism enclosed in said hollow body intermediate between said inlet aperture and waste outlet and above said waste outlet, a discharge valve of the flow-regulating type carried by said hollow body at a level below the comminuting mechanism, and means mounting said discharge valve for rotation between a fully open and an at least partially closed position dependent upon the relatively closed, opened and partially opened or closed condition of said waste input aperture as determined by said door.

6. A shredder according to claim 5, wherein the discharge valve is mounted in said waste outlet.

7. A shredder according to claim 5, wherein the discharge valve is mounted above the level of said waste outlet, said hollow body comprising means for connection with a duct below the level of the discharge valve and communicating with said waste outlet.

8. A shredder according to claim 5, wherein said input aperture door defines a vent aperture therein, and comprising a vent flap, mounted on said input aperture door, and means attached to the latter and to the vent flap for opening and closing the vent flap with respect to said door.

9. A shredder according to claim 5, comprising spray means directed inwardly of said hollow body and mounted therein adjacent the input aperture.

* * * * *